(12) United States Patent
Nanba et al.

(10) Patent No.: US 8,043,267 B2
(45) Date of Patent: Oct. 25, 2011

(54) PREFILLED SYRINGE

(75) Inventors: Ryohei Nanba, Osaka (JP); Masanobu Iwasa, Osaka (JP); Mitsuru Hasegawa, Osaka (JP); Yoshihisa Murai, Osaka (JP)

(73) Assignee: Nipro Corporation, Osaka (JP)

( * ) Notice: Subject to any disclaimer, the term of this patent is extended or adjusted under 35 U.S.C. 154(b) by 82 days.

(21) Appl. No.: 12/063,828

(22) PCT Filed: Aug. 18, 2006

(86) PCT No.: PCT/JP2006/316231
§ 371 (c)(1),
(2), (4) Date: Feb. 14, 2008

(87) PCT Pub. No.: WO2007/023736
PCT Pub. Date: Mar. 1, 2007

(65) Prior Publication Data
US 2009/0281504 A1    Nov. 12, 2009

(30) Foreign Application Priority Data

Aug. 22, 2005 (JP) ................. 2005-240137
Nov. 10, 2005 (JP) ................. 2005-325835

(51) Int. Cl.
*A61M 5/00* (2006.01)
*A61M 5/315* (2006.01)
(52) U.S. Cl. ......... 604/190; 604/222; 604/218; 604/231
(58) Field of Classification Search .............. 604/82, 604/190, 191, 200, 205, 218, 222, 93.01; 264/173.16
See application file for complete search history.

(56) References Cited

U.S. PATENT DOCUMENTS

| 3,149,717 | A |   | 9/1964  | Castelli |   |
|-----------|---|---|---------|----------|---|
| 3,468,471 | A |   | 9/1969  | Linder   |   |
| 3,503,497 | A |   | 3/1970  | Riely et al. | |
| 4,624,660 | A |   | 11/1986 | Mijers et al. | |
| 5,147,309 | A |   | 9/1992  | Hemmerich et al. | |
| 5,238,003 | A | * | 8/1993  | Baidwan et al. | 600/578 |
| 5,498,244 | A | * | 3/1996  | Eck | 604/198 |
| 6,183,464 | B1| * | 2/2001  | Sharp et al. | 604/533 |
| 6,544,233 | B1| * | 4/2003  | Fukui et al. | 604/191 |
| 2004/0267194 | A1 | * | 12/2004 | Sano et al. | 604/93.01 |
| 2005/0240159 | A1 | * | 10/2005 | Kito et al. | 604/222 |

FOREIGN PATENT DOCUMENTS

| EP | 0 687 477 A1 | 12/1995 |
| FR | 2 781 682 A1 | 2/2000 |
| JP | H07-289639 A | 11/1995 |
| JP | H11-332984 A | 12/1999 |
| JP | 2001-029466 A | 2/2001 |
| JP | 2002-315827 A | 10/2002 |
| JP | 2004-267662 A | 9/2004 |

\* cited by examiner

*Primary Examiner* — Theodore Stigell
*Assistant Examiner* — Imani Hayman
(74) *Attorney, Agent, or Firm* — Global IP Counselors, LLP (57) ABSTRACT

The prefilled syringe filled with a drug in advance, leaking of liquid from the cap is prevented, gas barrier properties are given to the whole of the barrel filled with the drug and the shoulder section so that degradation of the drug is prevented, permeation of microbial contaminants is prevented to a high extent, and efficiency of packing as a compact container can be increased. The prefilled syringe includes a guard-shaped extension projecting from the outer periphery of a shoulder section of the syringe barrel on the nozzle side, and a range from a part where a gasket of the plunger is positioned on the outer surface of the syringe barrel filled with the drug to the guard-shaped extension is covered with barrier packaging.

6 Claims, 8 Drawing Sheets

PREFILLED SYRINGE

CROSS-REFERENCE TO RELATED APPLICATIONS

This U.S. National stage application claims priority under 35 U.S.C. §119(a) to Japanese Patent Application No. 2005-240137, filed in Japan on Aug. 22, 2005, and Japanese Patent Application No. 2005-325835, filed in Japan on Nov. 10, 2005, the entire contents of which are hereby incorporated herein by reference.

BACKGROUND OF THE INVENTION

1. Field of the Invention

The present invention relates to a syringe (injection syringe) and particularly relates to a prefilled syringe that is already filled with a drug and is capable of injecting a patient at once simply by the fitting of an injection needle.

2. Background Information

Conventional so-called prefilled syringes where a syringe barrel of an injection syringe is filled with a drug in advance are well-known. Such prefilled syringes are equipped with a nozzle for fitting an injection needle at one end of a syringe barrel constituting a body of the syringe. At the other end, an opening is provided where a plunger having a gasket at a tip of a plunger rod can be freely moved backwards and forwards. After filling with a drug, the nozzle is usually covered over with a cap made of rubber in order to prevent leakage of the drug. The entire item is then blister-packed or pillow-packed with the plunger installed. Injection syringes prefilled with a drug where a nozzle covered with a cap is then covered with a heat-shrinkable resin film (shrink film) in order to prevent the cap from coming off as well as in order to prevent the filled drug from being tampered with have also been the subject of applications (for example, Japanese Patent Laid-Open Publication No. 2002-315827). However, when the syringe is made of plastic, it is necessary to store the syringe in barrier packing material having gas barrier properties in order to suppress deterioration of the drug filling the syringe barrel.

If the syringe is stored in a barrier packing material, the drug filling the syringe barrel does not degrade because of the gas barrier properties. However, the prefilled syringes are usually removed from the packaging beforehand in preparation in order to increase operation efficiency at the location of use such as a hospital and enable use at any time. There is, therefore, the problem that the drug will gradually degrade when left without use for a long period of time. When the barrier packaging is unwrapped and the syringe barrels that do not have gas barrier properties are left out, there is the fear of deterioration due to oxidation of the drug filling the barrel. Prefilled syringes provided with labels including inorganic compound deposition plastic film at 70% or more of the outer surface area of the barrel portion of the prefilled syringe have also already been filed (for example, Japanese Patent Laid-Open Publication No. 2004-267662).

Costs are also high when barrier packaging is used or when using barrier packaging in blister packaging or pillow packaging. Enclosure such as silica gel or ageless (registered trademark) (deoxidant) is also necessary in order to remove moisture and oxygen from within the packaging and this also invites high costs.

SUMMARY OF THE INVENTION

Even with a prefilled syringe that is filled with a drug in advance, it is possible to prevent the cap from coming off and to prevent leaking of the drug by covering the nozzle with the cap and covering both the cap and the nozzle with a shrink band. However, when the prefilled syringe is in an exposed state but the material of the syringe does not have gas barrier properties, oxygen permeates and it is not possible to prevent oxidation of the drug. Further, with prefilled syringes provided with labels of inorganic compound deposition plastic film at a surface area of 70 percent or more of the outside surface of the barrel portion of the prefilled syringe described above, the plastic film is not provided at a shoulder section from the barrel to the nozzle and the gas barrier properties therefore cannot be said to be complete. Moreover, during packaging of the prefilled syringes, fluid leakage, permeation of microbial contaminants, and deterioration of the drug is prevented to a high extent and it is also preferable to make the package small for ease of transport of a large number of syringes.

In order to resolve the above problems, it is the object of the present invention to provide a prefilled syringe where, even with a prefilled syringe filled with a drug in advance, leaking of liquid from the cap is prevented, gas barrier properties are given to the whole of the barrel filled with the drug and the shoulder section so that degradation of the drug is prevented, permeation of microbial contaminants is prevented to a high extent, and efficiency of packing as a compact container can be increased.

In order to achieve the aforementioned object, a first aspect of the invention is characterized by a prefilled syringe filled in advance with a drug within a syringe barrel, comprising a nozzle fitted with an injection needle, and an opening where a plunger, equipped with a gasket at an end of a plunger rod, freely moves backwards and forwards, wherein the prefilled syringe includes a guard-shaped extension projecting from the outer periphery of a shoulder section of the syringe barrel on the nozzle side, and a range from a part where a gasket of the plunger is positioned on the outer surface of the syringe barrel filled with the drug to the guard-shaped extension is covered with a barrier packaging. According to the aspect of the invention of claim 1 having the above structure, the outer surface of the syringe barrel filled with the drug is covered completely with barrier packaging. It is therefore possible to reliably prevent degradation of the drug.

A second aspect of the invention is characterized by a cap fitted to the end of the nozzle and the entire outer peripheral surface from the cap to the end of the extension is covered by a shrink film. According to the second aspect of the invention having the above structure, it is possible to completely prevent the cap coming off or coming loose, and peeling of barrier packaging of the extension for the shoulder section of the syringe barrel can be prevented.

A third aspect of the invention is characterized by a cap fitted to the end of the nozzle, and the whole of the outer peripheral surface of the syringe of a structure where the cap and the plunger are fitted is covered with a shrink film. According to the third aspect of the invention having the above structure, the whole of the syringe is covered with the shrink film. It is therefore possible to reliably prevent the plunger from coming off.

A fourth aspect of the invention is characterized by an air through-hole provided at a disc-shaped flange arranged at a base of the plunger rod, during covering of the whole syringe using the shrink film, the outer surface of the disc-shaped flange is exposed, and a filter member that is permeable to moisture is arranged at the outer surface side of the exposed disc-shaped flange so as to cover the air through-hole. According to the fourth aspect of the invention having the above structure, it is possible to prevent moisture from remaining in an internal space during high-pressure steam sterilization etc. even if the whole of the syringe is covered with the shrink film.

A fifth aspect of the invention is characterized by the surface of the disc-shaped flange is taken to be a duckboard-shaped uneven surface, with air through-hole provided at a recess. According to the fifth aspect of the invention having the above configuration, even if the filter member or shrink film is attached firmly to the disc-shaped flange, it is possible to ensure communicating paths via the air through-hole provided at the recess and passage of moisture can be achieved in a straightforward manner.

A sixth aspect of the invention is characterized by at least one first disc-shaped rib is provided projecting from a central part of the plunger rod and the air through-hole is provided at the disc-shaped rib. The outer diameter of the disc-shaped rib is of an order enabling passing through at the opening. According to the sixth aspect of the invention having the above structure, movement in an axial direction of the plunger rod is suppressed by covering and fixing the at least one projecting first disc-shaped rib using shrink film. It is therefore possible to prevent the plunger rod from coming off and it is possible to prevent the plunger rod from being pushed into the syringe barrel. Further, this enables transportation and storage in a packaged state as single units. External packaging such as blister packaging is therefore not necessary and storage space savings can be made.

A seventh aspect of the invention is characterized by at least one second disc-shaped rib is provided in a projecting manner in the vicinity of the base of the syringe barrel. According to the seventh aspect of the invention having the above structure, the at least one second disc-shaped rib is attached firmly using shrink film. It is therefore possible to reliably prevent microbial contaminants likely to permeate in from the nozzle fitted with the cap to permeate in the plunger direction.

An eighth aspect of the invention is characterized by a lid member having the filter member is fitted at the disc-shaped flange. According to the eighth aspect of the invention having the above configuration, changing of the filter member is straightforward, and the selection and use of filter members with arbitrary characteristics is possible. The shape of the lid member can also be arbitrarily selected compared to the disc-shaped flange and a shape where adhesion with the shrink film is superior can therefore be adopted.

A ninth aspect of the invention is characterized by the shrink film is attached firmly to the first disc-shaped rib and the second disc-shaped rib so that the whole of the syringe is covered and the shrink film is heat-shrinked by heating during high-pressure sterilization. According to the ninth aspect of the invention having the above structure, the whole of the syringe is covered with shrink film at the same time as sterilization. It is therefore possible to form syringe packaging enabling a high-degree of prevention of permeation of microbial contaminants to within the syringe.

According to the present invention, even with a prefilled syringe filled with a drug in advance, it is possible to prevent leaking of liquid from the cap, gas barrier properties are given to the whole of the barrel filled with the drug and the shoulder section so that degradation of the drug can be prevented, and permeation of microbial contaminants can be prevented to a high extent. Further, compact packaging where the whole of the outer surface of the entire syringe is covered in shrink film can be achieved. It is therefore possible to keep the syringes in single syringe units, and prefilled syringes where packaging efficiency is improved can be obtained. The problem of gradual deterioration of the drug is also prevented even when the drug is left for a long time without being used.

There is also no fear of the plunger coming out as the result of the inadvertent application of force to the plunger rod or of the plunger gasket moving and the drug leaking out before the shrink film is removed for use. Prefilled syringes that can be kept in single syringe units and where the packaging efficiency is increased can therefore be obtained. Further, there is no distinguishing of upper and lower surfaces as with blister packaging and as the syringe and shrink film are in close proximity, visibility in an outer-packed state is improved. In addition, the present invention substantially reduces the amount (volume etc.) of waste for outer packaging at the time of disposal in comparison to blister packaging etc.

BRIEF DESCRIPTION OF THE DRAWINGS

FIG. 1 shows a prefilled syringe of a first embodiment according to the present invention where (a) is a plan view, and (b) is a side cross-sectional view.

FIG. 2 shows a prefilled syringe 1B of a second embodiment, where (a) is a plan view, (b) is a side cross-sectional view, and (c) is a side view.

FIG. 4 shows a prefilled syringe 1C of a third embodiment, where (a) is a plan view, (b) is a side cross-sectional view, and (c) is a side view.

FIG. 5 shows a cross-sectional view of a prefilled syringe 1C of the third embodiment, where (a) is a view representing from arrow direction B1-B1 and (b) is a view representing from arrow direction A2-A2.

FIG. 6 shows a prefilled syringe 1D of the second embodiment, where (a) is a plan view, (b) is a side cross-sectional view, and (c) is a side view.

FIG. 7 shows a cross-sectional view of a prefilled syringe of the forth embodiment, where (a) is a view representing from arrow direction B2-B2 and (b) is a view representing from arrow direction A3-A3.

FIG. 8 shows a view representing a embodiment of being directly adhered a filter member to the disc-shaped flange, where (a) is a side cross-sectional view of a base of a plunger rod, and (b) is a view representing the above from arrow direction A4-A4.

DETAILED DESCRIPTION OF THE PREFERRED EMBODIMENTS

Figure 1A:
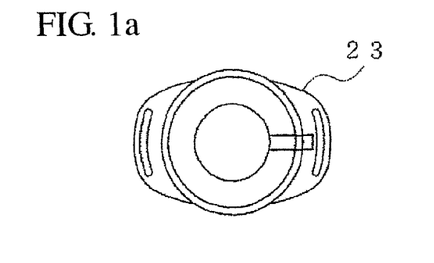
Figure 1B:
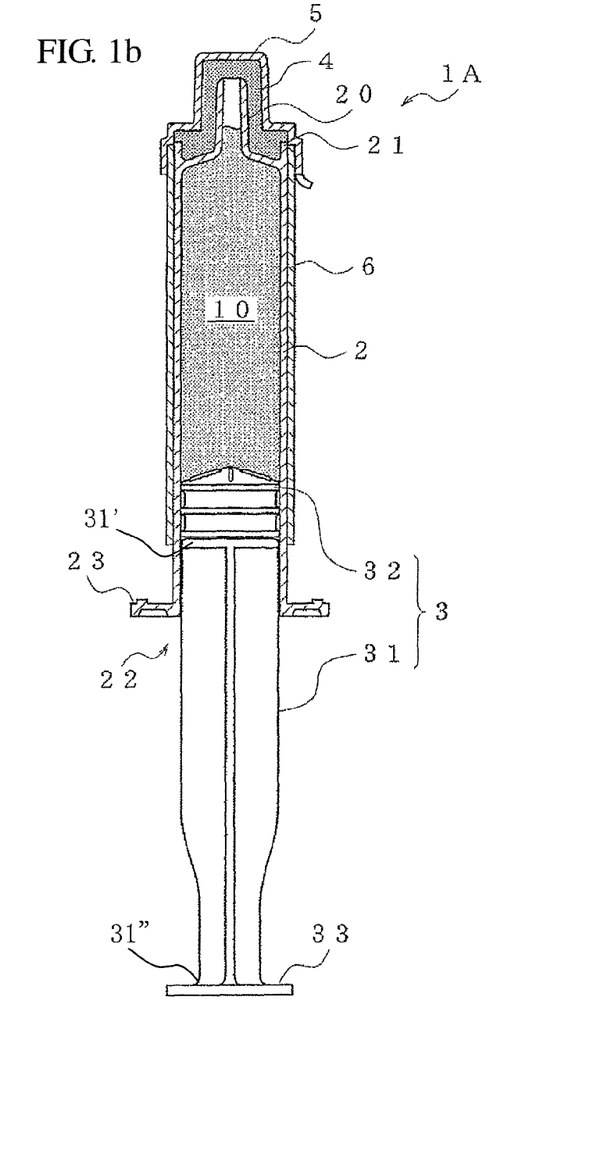

The following is a detailed description of embodiments of a prefilled syringe of the present invention based on FIG. 1 to FIG. 8. First, a description is given of a first embodiment of a prefilled syringe of the present invention using FIG. 1. A prefilled syringe 1A filled with a drug and covered in barrier packaging is shown in FIG. 1, where (a) is a plan view, and (b) is a side cross-sectional view.

The prefilled syringe 1A is equipped with a syringe barrel 2 filled with a drug 10 and a plunger 3. The plunger 3 is equipped with a plunger rod 31 and a gasket 32 provided at a tip end 31' (the first end) of the plunger rod 31. The syringe barrel 2 is equipped with a nozzle 20 capable of being fitted with an injection needle etc., and an opening 22 that the plunger 3 can freely move within. Further, a grip 23 is formed projecting from the periphery of the tip of the opening 22. As shown in the plan view, the grip 23 is an ellipsoidal plate-shaped projection. This therefore gives a shape that is easy for a person to grip while the disc-shaped flange 33 formed at a base end 31" (the second end) of the plunger 3 is pushed in so that the plunger 3 moves within the syringe barrel 2.

A cap 4 is then fitted to the tip of the nozzle 20 and is sealed in a fluid-tight manner so that the filled drug 10 does not leak out. It is also possible to cover the whole of the outer periphery of the cap 4 with the shrink film 5. In order to prevent the cap 4 inadvertently coming off or coming loose, from the cap 4 to the tip of the syringe barrel 2 is covered in a shrink film 5.

Further, the outer surface of the syringe barrel 2 filled with the drug is covered with barrier packaging 6 so as to suppress deterioration of the drug. During this time, in order to reliably cover the entire outer surface of the syringe barrel 2, a guard-shaped extension 21 is provided projecting from the outer periphery of a shoulder section of the syringe barrel on the side of the nozzle 20. A range spanning from a part where the gasket 32 of the plunger with the plunger 3 fitted is positioned to a guard-shaped extension 21 is covered by the barrier packaging 6. Covering from the base end of the gasket 32 is preferable.

Moreover, the shrink film 5 covers up to the tip of the barrier packaging 6. Gas barrier packaging with superior transparency such as enables filling with a drug to be confirmed and that provides a barrier to oxygen in order to prevent oxidation of the drug is preferable as the barrier packaging 6. Further, the barrier packaging 6 simply covers the outer periphery of the cylindrical syringe barrel 2 and flexibility is not taken to be important.

The prefilled syringe 1A of the above structure is such that filled drug 10 does not degrade or leak out and can therefore be taken out and kept one at a time. This contributes to an increase in operation efficiency when used at locations such as hospitals and to reduction of storage space. The shrink film 5 can cover not just the syringe tip that the cap 4 is installed at but can also cover the whole of the syringe including the plunger 3 in an integrated manner. A prefilled syringe 1B of this structure is described using FIG. 2.

Figure 2A:
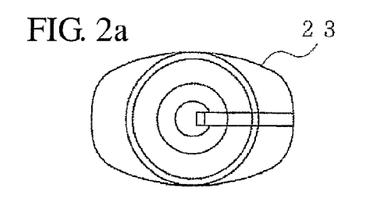
Figure 2B:
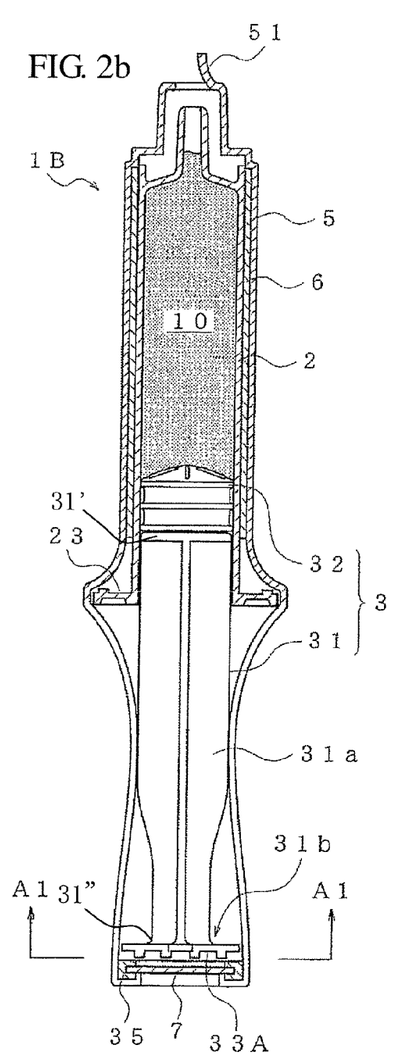
Figure 2C:
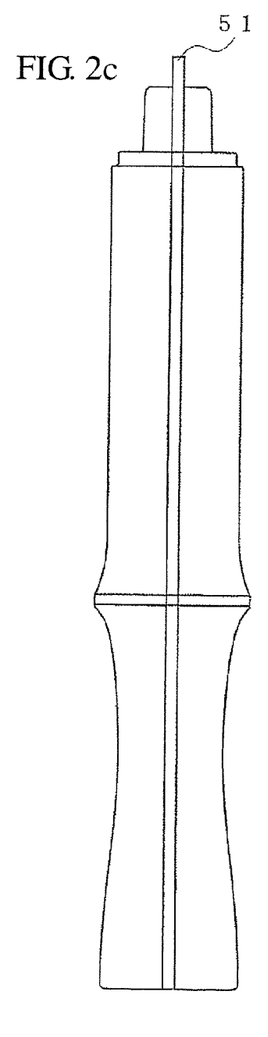

The prefilled syringe 1B of a second embodiment is shown in FIG. 2, where (a) is a plan view and (b) is a side cross-sectional view, and (c) is a side view. The prefilled syringe 1B having the syringe barrel 2 filled with the drug 10 and the plunger 3 having the plunger rod 31 and the gasket 32 is the same as described above for the prefilled syringe 1A. Further, the shrink film 5 is made so as to cover the whole of the syringe including the plunger 3 in an integrated manner. As a result, not only is coming off and loosening of the plunger 3 prevented, but it is also made difficult for outside air to permeate to within the syringe 2 and microbial contaminants also cannot permeate. This increases the degree of safety.

However, when a method using, for example, high-pressure steam sterilization is adopted at the time of thermally shrinking of the shrink film 5, there is the fear that moisture of an air-tight space will condense and remain within the space. In this embodiment, the structure is such that a base end 31b of the plunger rod 31 is made in the shape of a duckboard, with a filter member 7 having moisture permeability so that moisture passes through but microbial contaminants do not interposed there between. Making the base end 31b of the plunger rod 31 the shape of a duckboard is in order to ensure a communicating path moisture in the air-tight space can permeate through. As a result, in this embodiment, the surface is a structure (refer to FIG. 3) where air through-holes 34 are provided at recesses of an undulating surface of a disc-shaped flange 33A with a duckboard-shaped surface. This means that even if the filter member 7 is adhered to the disc-shaped flange 33A, contacting takes place only with the convex parts of the disc-shaped flange 33A and not with the air through-holes 34.

Figure 3:
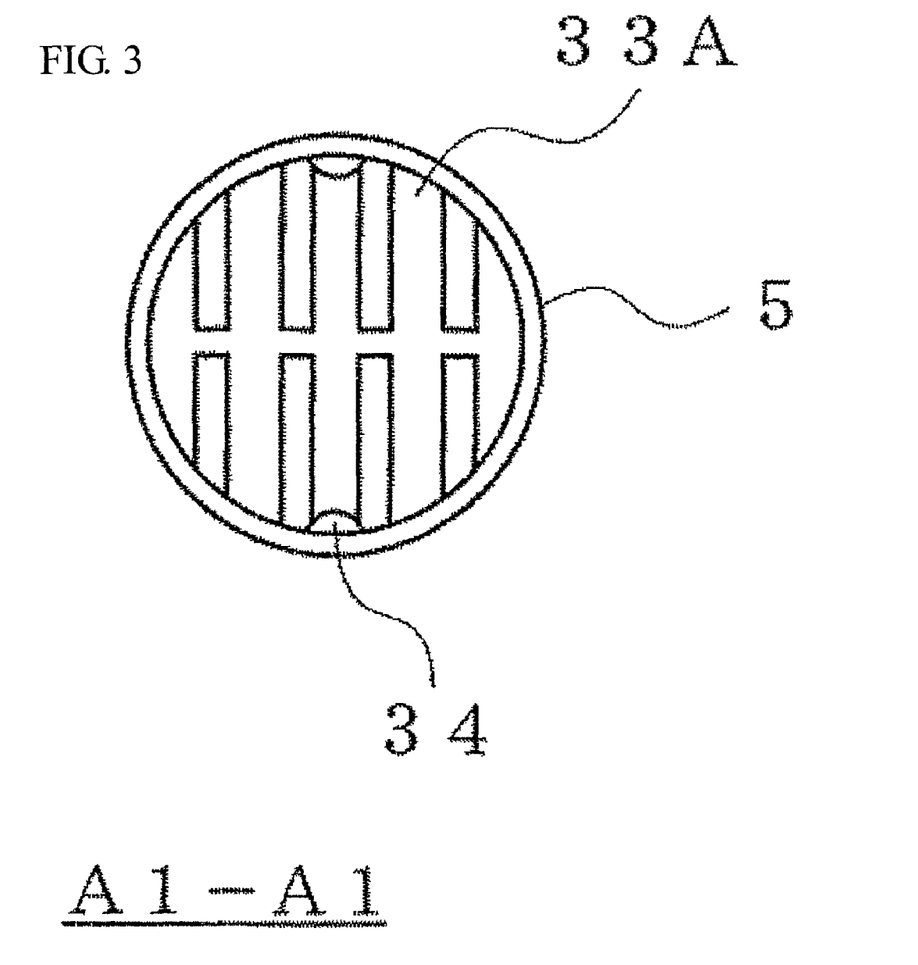
FIG. 3 shows a view representing from arrow direction of the prefilled syringe according to the second embodiment.

This means that even if, for example, the air through-holes 34 are small, the filter member 7 is not attached directly and the spaces before and after the through-holes communicate with each other. A communicating path that moisture of the air-tight space can pass through can therefore be ensured. Tyvek (registered trademark of Dupont) unwoven cloth sheets where continuous very fine fibers of polyethylene of, for example, 0.5 to 1 microns are subjected to high-temperatures so as to be bonded is preferably utilized as the filter member 7. It is also possible to use other sterilized paper that is permeable to moisture. The plunger rod 31 constituting the plunger 3 may be formed by arranging a disc-shaped flange at a small-diameter rod. However, as in this embodiment, it is also possible to provide sleeves 31a projecting in a radial direction at a plurality of locations in a circumferential direction of a center axis of a small diameter. With this configuration, large air-tight spaces are formed between neighboring sleeves 31a when the entirety is covered by the shrink film 5. A structure is therefore adopted where the filter member 7 for moisture sealed within the spaces to pass through is provided at the disc-shaped flange 33A of the plunger rod base.

Figure 8A:
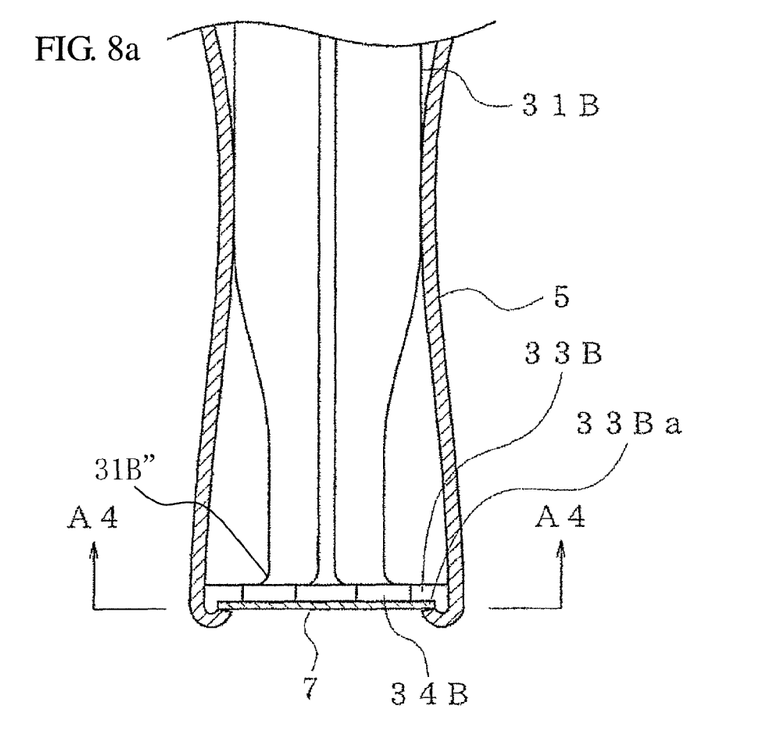
Figure 8B:
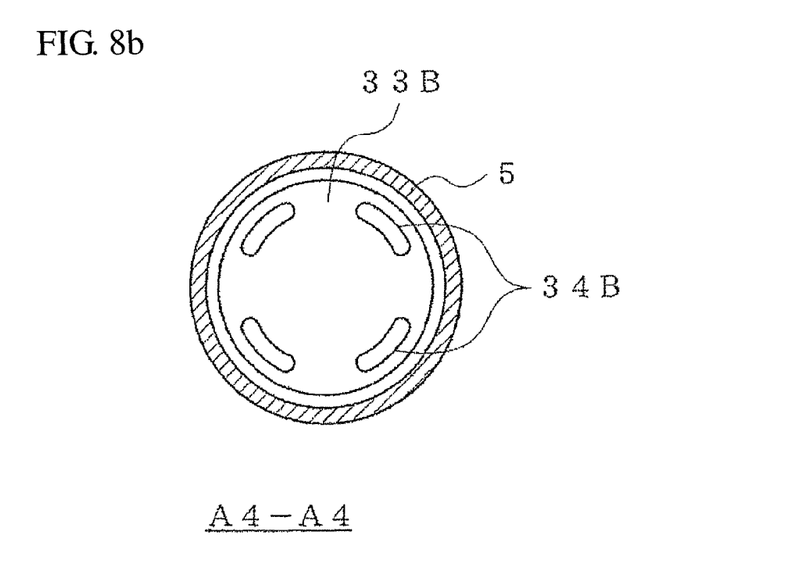

Namely, as shown in FIG. 3, a structure is adopted where air through-holes 34 are provided at the disc-shaped flange 33A and the filter member 7 that allows moisture to pass through but that does not allow microbial contaminants to pass is fitted at the outside. It is sufficient for the air through-holes 34 to be provided at at least one location at the disc-shaped flange 33A but if a structure where a plurality are provided is adopted, it is preferable for passing through of the moisture to take place rapidly. In the above, a structure may be adopted that is covered on top by the shrink film 5 (refer to FIG. 8) as the structure for directly mounting the filter member 7 at the disc-shaped flange 33A. However, adopting a structure where a lid member 35 supporting the filter member 7 is arranged at the outside of the disc-shaped flange 33A with the top then being covered by the shrink film 5 is preferable because selection and mounting of the filter member 7 having predetermined functions is straightforward. The shape of the lid member 35 can also be arbitrarily selected compared to the disc-shaped flange and a shape where adhesion with the shrink film is superior can therefore be adopted. In addition, it is also possible to provide an uneven surface or air through-holes at an outer peripheral edge of the disc-shaped flange 33A and the surface of the base or to enable the shrink film 5 to become wrinkled, in order to ensure a communicating path when the shrink film 5 is heat-shrunk in advance in order to cover the outer edge of the disc-shaped flange 33A. The lid-shaped filter member 7 that allows moisture to permeate but does not allow microbial contaminants to permeate can then be fitted at the disc-shaped flange 33A in such a manner as to include the boundary of the disc-shaped flange 33A and the shrink film 5.

Numeral 51 denotes a pull-tag for opening use. The shrink film 5 can then be opened by holding the pull-tag 51 and tearing the pull-tag 51 in a strip shape. Next, a description is given of a prefilled syringe 1C of a third embodiment provided with a plunger rod having disc-shaped ribs projecting in a radial direction using FIG. 4.

Figure 4A:
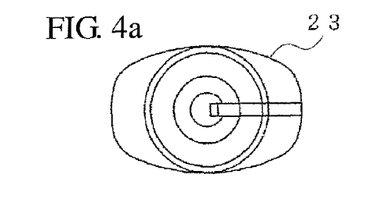
Figure 4B:
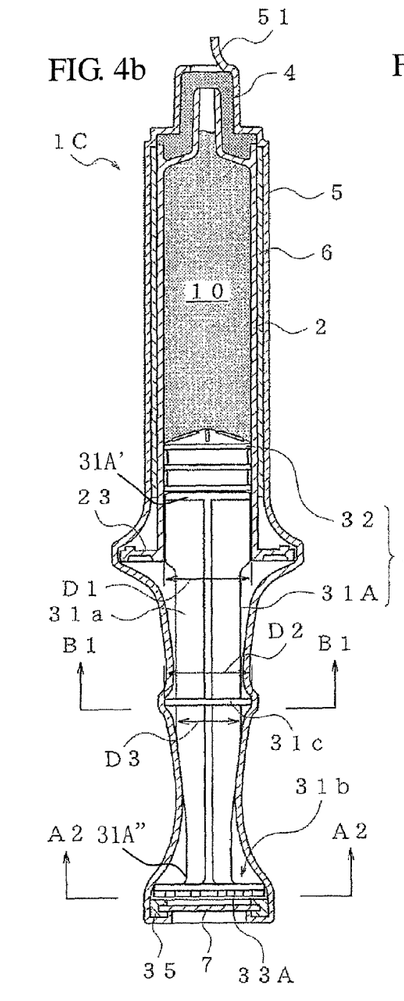
Figure 4C:
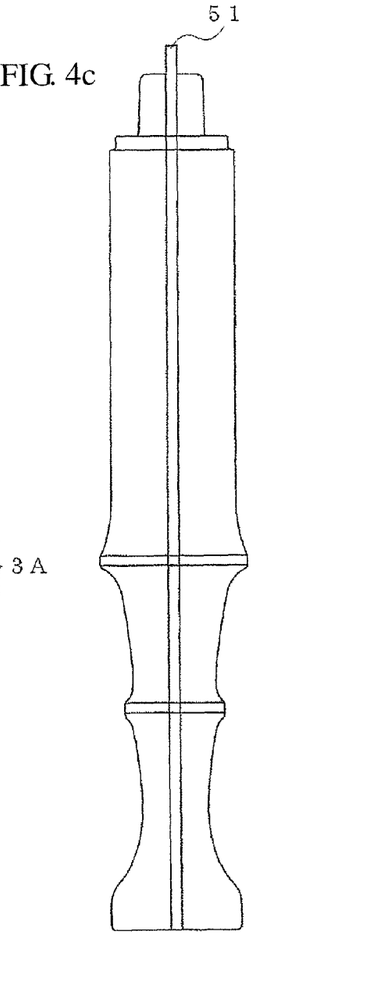

The prefilled syringe 1C of the third embodiment is shown in FIG. 4, where (a) is a plan view and (b) is a side cross-sectional view, and (c) is a side view. The prefilled syringe 1C is equipped with the syringe barrel 2 filled with the drug 10 and a plunger 3A. Further, the plunger 3A has a plunger rod 31A and the gasket 32 provided at a tip end 31A' (the first end) of the plunger rod 31A. The shrink film 5 covering the whole of the syringe including the plunger 3A in an integrated manner, providing the air through-holes 34 at the disc-shaped flange 33A formed at a base end 31A" (the second end) of the plunger rod 31A, and fitting the filter member 7 are the same as for the prefilled syringe 1B. However, the adopted configuration is such that a first disc-shaped rib 31c projecting in a radial direction is provided at a central part of the plunger rod 31A constituting the plunger 3A. The disc-shaped rib 31c is inserted within the syringe barrel 2. Dimensions are therefore adopted where an outer diameter D2 of the disc-shaped rib 31c is smaller than an inner diameter D1 of the syringe barrel 2.

Because of this, an external diameter D3 of a sleeve part of the plunger rod 31A is given a smaller diameter and a stepped shape. The disc-shaped rib 31c positioned at a central part of the plunger rod 31 therefore has a projecting external shape when the shrink film 5 covers the whole of the syringe including the plunger 3A in an integrated manner. If the above configuration is adopted, it is possible to suppress movement in an axial direction of the plunger 3A using the shrink film 5 attached firmly so as to be fixed to the projecting first disc-shaped rib 31c. Namely, the position of the plunger 3A is fixed and does not move even if pushed or pulled. It is therefore possible to reliably prevent the filled drug 10 from leaking out. The prefilled syringe 1C of this embodiment is capable of being transported and stored as is and outer packaging such as blister packaging is unnecessary. It is therefore possible to save on storage space.

Figure 5A:
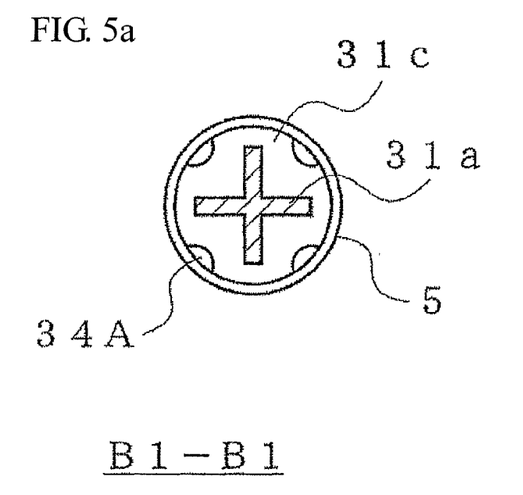
Figure 5B:
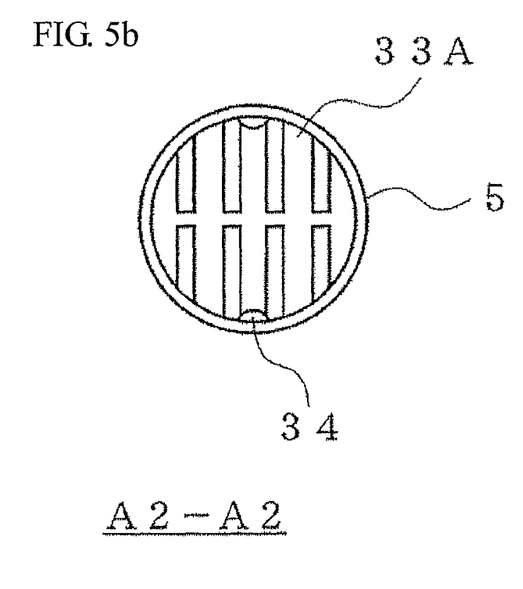

By adopting the above configuration, when the pull-tag 51 for opening is gripped in a motionless manner prior to opening and a strip shape is torn so as to open the shrink film 5, the plunger rod 31A can easily be pushed into the syringe barrel 2. As shown in FIG. 5(a), first disc-shaped rib 31c has a circular cross-section. When covered with the shrink film 5, this is reliably attached firmly to this circular outer shape and the inside is sealed to a high extent.

The air through-holes 34 that are capable of allowing moisture enclosed in the space to pass through are provided at the first disc-shaped rib 31c. According to this structure, it is possible for moisture to escape via the filter member 7 from the air through-holes 34A provided at the disc-shaped rib 31c and the air through-holes 34 (refer to FIG. 5(b)) provided at the disc-shaped flange 33A even if a structure provided with the first disc-shaped rib 31c at this central part is adopted for the plunger rod 31A. Next, a description is given of a prefilled syringe 1D of a fourth embodiment provided with a projecting disc-shaped rib in the vicinity of the base of the syringe barrel using FIG. 6.

Figures 6A, 6B, 6C:
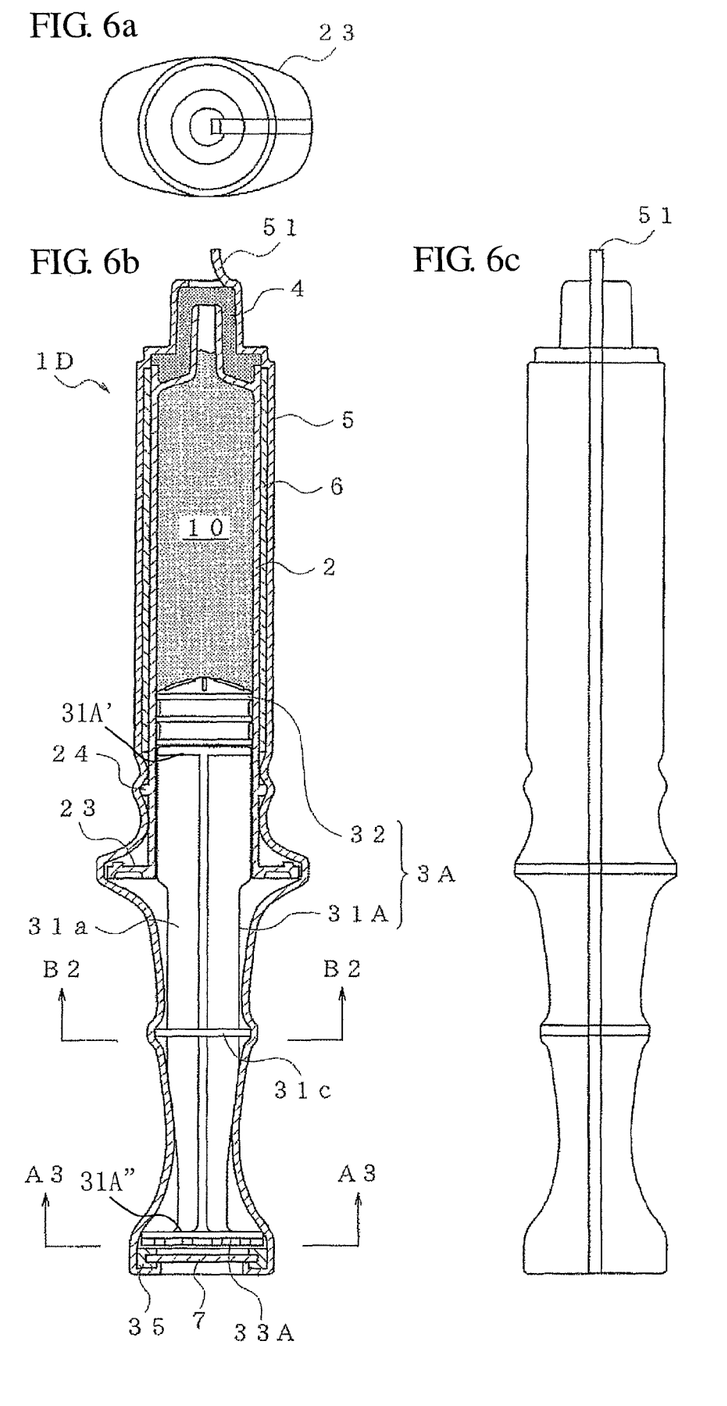

The prefilled syringe 1D of the fourth embodiment is shown in FIG. 6, where (a) is a plan view, (b) is a side cross-sectional view, and (c) is a side view. The prefilled syringe 1D is an example where, in addition to the prefilled syringe 1C described above, a second disc-shaped rib 24 is provided in the vicinity of the base close to the grip 23 of the syringe barrel 2. The basic structure relating to the syringe body is the same as for the prefilled syringe 1C and is not described here. It is also possible to provide a plurality of second disc-shaped ribs 24.

If the prefilled syringe 1D of the above configuration is adopted, the shrink film 5 is attached firmly so as to be fixed to the projecting second disc-shaped rib 24. It is therefore possible to reliably prevent microbial contaminants etc. from infiltrating from the nozzle tip the cap 4 is fitted to and a more desirable structure is achieved. There is also the benefit that even if the pull-tag 51 for opening use is grasped and torn in a strip-shape so as to open the shrink film 5 with the syringe then being taken out, microbial contaminants do not become attached to the grip 23 or the plunger rod 31A. There is therefore the further benefit that there is no fear of microbial contaminants infiltrating into the filled drug 10.

Figure 7A:
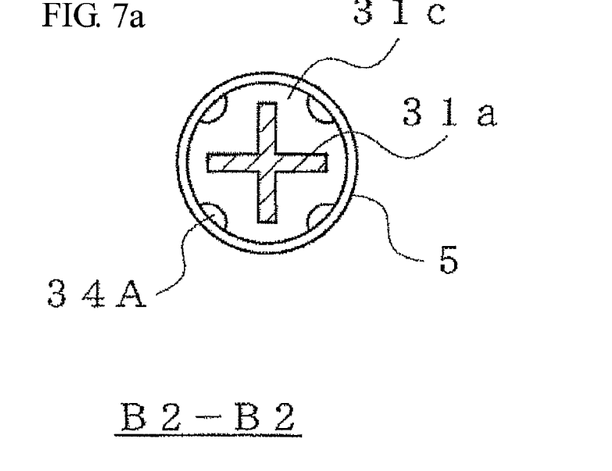
Figure 7B:
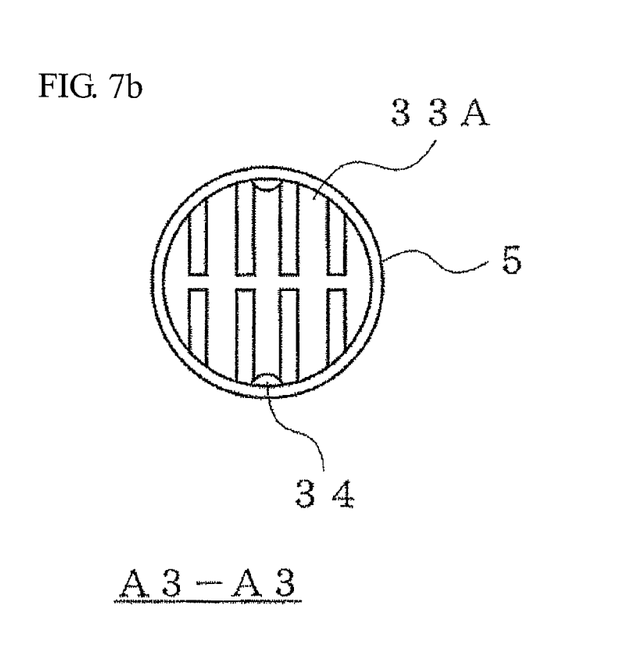

FIG. 7(a) is a cross-sectional view of the disc-shaped rib 31c, and FIG. 7(b) is a cross-sectional view of a disc-shaped flange 33. Both have a circular cross-section and are shown to have a plurality of air through-holes 34 and 34A. The filter member 7 is set at the outer side of the disc-shaped flange 33A via the lid member 35. However, it is also possible for the filter member 7 to be directly mounted at the disc-shaped flange 33A as described above and an example of this structure is described using FIG. 8.

An example where the filter member 7 is directly mounted at the disc-shaped flange is shown in FIG. 8, where (a) is a side cross-sectional view of the plunger rod base and (b) is a view along arrows A4-A4 of the previous drawing. The plunger rod 31B shown in the drawing is provided with a disc-shaped flange 33B having air through-holes 34B at its base end 31B" (the second end), with the filter member 7 being directly applied to the outer side of the disc-shaped flange 33B.

During this time, if a structure is adopted where a recess 33Ba is provided for fitting the filter member 7 to the outer side of the disc-shaped flange 33B, it is preferable for the filter member 7 to be reliably mounted at a normal position. The shape of the air through-holes 34B is by no means particularly limited, and the air through-holes 34B can be a plurality of ellipsoidal holes as shown in FIG. 8(b) or can be circular holes. It is also preferable for the air through-holes to have a surface area of an order enabling moisture in the air-tight space formed by sealing during covering the whole in shrink film 5 to pass rapidly.

As described above, the filter member 7 is a film that is permeable to moisture and suppresses the passage of microbial contaminants. This means that moisture does not remain and can be eliminated even when the syringe is covered entirely by the shrink film 5. As a result, even if moisture remains within the sealed space, this moisture can be rapidly eliminated while shrinking the shrink film 5 that is heat-shrinkable resin film utilizing heat at the time of, for example, high-pressure steam sterilization. Further, microbial contaminants also do not permeate into the sterilized sealed space from outside. This means that it is possible to guarantee the sterility of the syringe right up to immediately before use and it is therefore possible to form syringe containing packaging where permeation of microbial contaminants into the syringe can be prevented to a high extent.

As described above, according to the prefilled syringe of the present invention, it is possible to reliably prevent degradation of a drug filled in advance. Further, keeping of single packed syringes is possible, handling is straightforward, and storage space savings can be made. Further, it is possible to prevent permeation of microbial contaminants into a sterilized sealed space from outside to a high extent. This means that use with peace of mind is possible and that a prefilled syringe with superior ease of use can be obtained.

Moreover, it is also possible for the present invention to give the shrink film color in order to block light under the assumption that there will be cases such as the syringe barrel element being in the light while being kept so that radicals are formed and degradation due to oxidation takes place, the case of elution in medicinal solution, or in the case that a medicinal solution has photodegradative properties.

The invention claimed is:
1. A prefilled syringe filled with a drug comprising:
a hollow cylinder having a nozzle coupled to an opening of the cylinder at a first end and configured to be fitted with an injection needle, and a guard-shaped extension proximate to the nozzle and axially projecting from a shoulder section of the cylinder;

a plunger having a plunger rod and a gasket fixedly coupled to a first end of the plunger rod, the plunger arranged to freely move backwards and forwards within the opening of the cylinder at a second end, the plunger rod including a disc-shaped flange at a second end of the plunger rod with the disc-shaped flange having at least one air through-hole;

a barrier package that covers the peripheral surface of the cylinder between the first end thereof proximate to the guard-shaped extension and the second end thereof proximate to the opening;

a cap fitted onto an end of the nozzle;

a filter member that is permeable to moisture, the filter member being arranged adjacent to an outside surface of the disc-shaped flange of the plunger so as to cover the air through-hole; and a shrink film that covers the outer peripheral surface of the barrier package, the cap fitted onto the nozzle and the plunger with the filter member being at least partially exposed such that moisture enclosed in a space formed between the shrink film and an outer surface of the plunger rod is released outside of the shrink film through the air through-hole and the filter member, the shrink film including a pull-tag arranged to be pulled to tear the shrink film.

2. The prefilled syringe according to claim 1, wherein the outer surface of the disc-shaped flange has an undulating surface, the undulating surface includes a recess with the air through-hole.

3. The prefilled syringe according to claim 1, wherein the plunger rod further includes a first disc-shaped rib projecting from a central part thereof, the first disc-shaped rib has at least one air through-hole.

4. The prefilled syringe according to claim 3, wherein the hollow cylinder further having at least one second disc-shaped rib projecting from the outer peripheral surface of the cylinder.

5. The prefilled syringe according to claim 1, further comprising:

a lid member that supports the filter member, the lid member is arranged on the outside surface of the disc-shaped flange.

6. The prefilled syringe according to claim 4, wherein the shrink film is heat-shrunk and firmly attached to the first disc-shaped rib and the second disc-shaped rib so as to cover the entire prefilled syringe.

\* \* \* \* \*